US009728001B2

(12) United States Patent
Koenig (10) Patent No.: US 9,728,001 B2
(45) Date of Patent: Aug. 8, 2017

(54) PROCESSING AND RENDERING OF LARGE IMAGE FILES

(75) Inventor: Florian Koenig, Quebec (CA)

(73) Assignee: Real-Scan, Inc., Seattle, WA (US)

( * ) Notice: Subject to any disclaimer, the term of this patent is extended or adjusted under 35 U.S.C. 154(b) by 122 days.

(21) Appl. No.: 13/477,942

(22) Filed: May 22, 2012

(65) Prior Publication Data

US 2013/0076747 A1    Mar. 28, 2013

Related U.S. Application Data

(60) Provisional application No. 61/538,281, filed on Sep. 23, 2011.

(51) Int. Cl.
| | | |
|---|---|---|
| *G06T 15/00* | (2011.01) | |
| *G06T 17/00* | (2006.01) | |
| *G06T 15/40* | (2011.01) | |
| *G06T 15/08* | (2011.01) | |
| *A61B 6/03* | (2006.01) | |
| *A61B 6/00* | (2006.01) | |
| *A61B 5/00* | (2006.01) | |

(52) U.S. Cl.
CPC ............. *G06T 15/40* (2013.01); *A61B 6/03* (2013.01); *A61B 6/52* (2013.01); *A61B 6/5223* (2013.01); *A61B 6/5294* (2013.01); *A61B 6/563* (2013.01); *G06T 15/08* (2013.01); *A61B 5/0013* (2013.01); *G06T 2210/32* (2013.01); *G06T 2210/41* (2013.01); *G06T 2210/52* (2013.01)

(58) Field of Classification Search
CPC ......... G06T 15/00; G06T 17/00; G06T 15/40; G06T 2210/32; G06T 2210/41; G06T 2210/52; A61B 5/0013; A61B 6/03; A61B 6/52; A61B 6/5223; A61B 6/5294; A61B 6/563
USPC ....... 345/419, 420, 424, 501, 502, 505, 522, 345/536, 555, 557
See application file for complete search history.

(56) References Cited

U.S. PATENT DOCUMENTS

| | | | | |
|---|---|---|---|---|
| 6,259,815 | B1 * | 7/2001 | Anderson | G06K 9/6206 382/218 |
| 6,559,843 | B1 * | 5/2003 | Hsu | G06T 15/40 345/421 |
| 8,295,620 | B2 * | 10/2012 | Ernvik | G06T 19/00 382/128 |
| 2004/0170311 | A1 * | 9/2004 | Accomazzi | G06T 15/20 382/131 |
| 2006/0031372 | A1 * | 2/2006 | Krishnan et al. | 709/207 |
| 2006/0056680 | A1 * | 3/2006 | Stutsman | G06T 15/08 382/154 |
| 2007/0165026 | A1 * | 7/2007 | Engel | G06T 15/08 345/424 |
| 2008/0298470 | A1 * | 12/2008 | Boyce | H04N 19/61 375/240.27 |
| 2009/0284537 | A1 * | 11/2009 | Hong | G06T 1/60 345/522 |

(Continued)

*Primary Examiner* — Gregory J Tryder
*Assistant Examiner* — Michael Le
(74) *Attorney, Agent, or Firm* — Lee & Hayes, PLLC; Benjamin A. Keim (57) ABSTRACT

Tomographic data representing an imaged three-dimensional object is divided into macro blocks and filtered by visibility and presence in a projected frame of a rendered three-dimensional object to speed rendering of the object. The data are loaded and rendered in parallel for improved speed and capacity.

16 Claims, 7 Drawing Sheets

(56) References Cited

U.S. PATENT DOCUMENTS

| | | | |
|---|---|---|---|
| 2010/0079456 A1* | 4/2010 | Barth | 345/424 |
| 2010/0091836 A1* | 4/2010 | Jia | H04N 19/44 |
| | | | 375/240.01 |
| 2011/0234583 A1* | 9/2011 | Bakalash | 345/419 |

* cited by examiner

COMPUTING DEVICE
106

PROCESSING AND RENDERING OF LARGE IMAGE FILES

CROSS-REFERENCE TO RELATED APPLICATION

This application claims the benefit of U.S. Provisional Application No. 61/538,281, filed Sep. 23, 2011, which is expressly incorporated herein by reference in its entirety.

BACKGROUND

Three-dimensional objects may be represented as a stack of two-dimensional images. X-ray computed tomography (CT) is one imaging technology that uses multiple two-dimensional images to represent three-dimensional objects. CT scanning employs tomography to image two-dimensional slices of an object and create a three-dimensional image from the two-dimensional slices by computer processing. Magnetic resonance imaging (MRI) is another imaging technology that uses multiple two-dimensional images to represent a three-dimensional object.

Images generated by CT scanning can provide high-contrast resolution that shows physical density differences of less than one percent. A large series of two-dimensional X-ray images taken around a single axis of rotation and digital geometry processing may be used to generate a three-dimensional image from the two-dimensional images. CT scanning is commonly used for medical applications, but is also used in engineering applications as a technique for nondestructive materials testing and in archaeological applications for imaging the contents of artifacts. The two-dimensional images generated by CT scanning (or another imaging technique) may be formatted as DICOM, TIFF, BMP, JPEG, or another file type.

Although computer systems exist for creating three-dimensional images from a series of CT scans, these systems are expensive, create large digital files that are difficult to transfer or share, and thus, limit access to three-dimensional representations of CT scans. Accordingly, many healthcare professionals have relied on two-dimensional CT scan images and generic models for both their own analysis and for presentation to patients. Sharing CT scan data, to receive a second opinion for example, is typically conducted by printing out images from a two-dimensional or three-dimensional rendering or transporting a large volume of data (e.g., on an optical disk) that requires a specialized computer to view.

Thus, access and usability of CT scan data, as well as other types of data (e.g., MRI images) consisting of two-dimensional image "slices" of a three-dimensional object, could be improved by techniques that make advanced renderings of a stack of two-dimensional images easily available.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Overview

This disclosure describes, in part, techniques for rendering an ordered series of two-dimensional images, a "stack" of images, to create a three-dimensional solid model. Techniques described herein allow for efficient generation of three-dimensional models and provide a convenient user interface for manipulating those models through an economical web-browser interface.

The techniques include efficient parallelized loading of large data sets that comprise a series of two-dimensional slices of an imaged three-dimensional object, and efficient parallelized rendering of two-dimensional projections of the three-dimensional object. The two-dimensional images may be formatted as Digital Imaging and Communications in Medicine (DICOM), Tagged Image File Format (TIFF), bitmap (BMP), Joint Photographic Experts Group (JPEG), Portable Network Graphics (PNG), or another type of image file. In addition to processing image stacks received from a CT scan or an MRI scan, it is also within the scope of the techniques covered in this disclosure to received data that is already formatted as three-dimensional data such as a three-dimensional volume of voxels (e.g., from a DICOM 3D file, a virtual computer simulation, etc.). Furthermore, the input data for the systems and processes described herein may also be four-dimensional volume data that can be treated as a set of three-dimensional voxel volumes.

The input data may be read into Volumetric Picture Elements (voxels) and divided into a large number of macro blocks, and the macro blocks may be saved to files on separate hard drives. Each voxel is associated with a value representing its level of opacity. The macro blocks include attributes that summarize the maximum and minimum opacity values of constituent voxels. Voxels within certain range of opacity values are potentially visible in a rendered projection of the object. Note that macro blocks may include numerous other types of attributes, such as, for example, information about the color ranges of constituent voxels. The macro blocks may be checked for visibility and whether they are in a viewing frame by testing the attributes. Macro blocks that are visible and in-frame are provided to the graphics processor, to have their constituent voxels loaded from the hard disks in parallel and rendered in parallel into a projection of the object.

Illustrative Architecture

Figure 1:
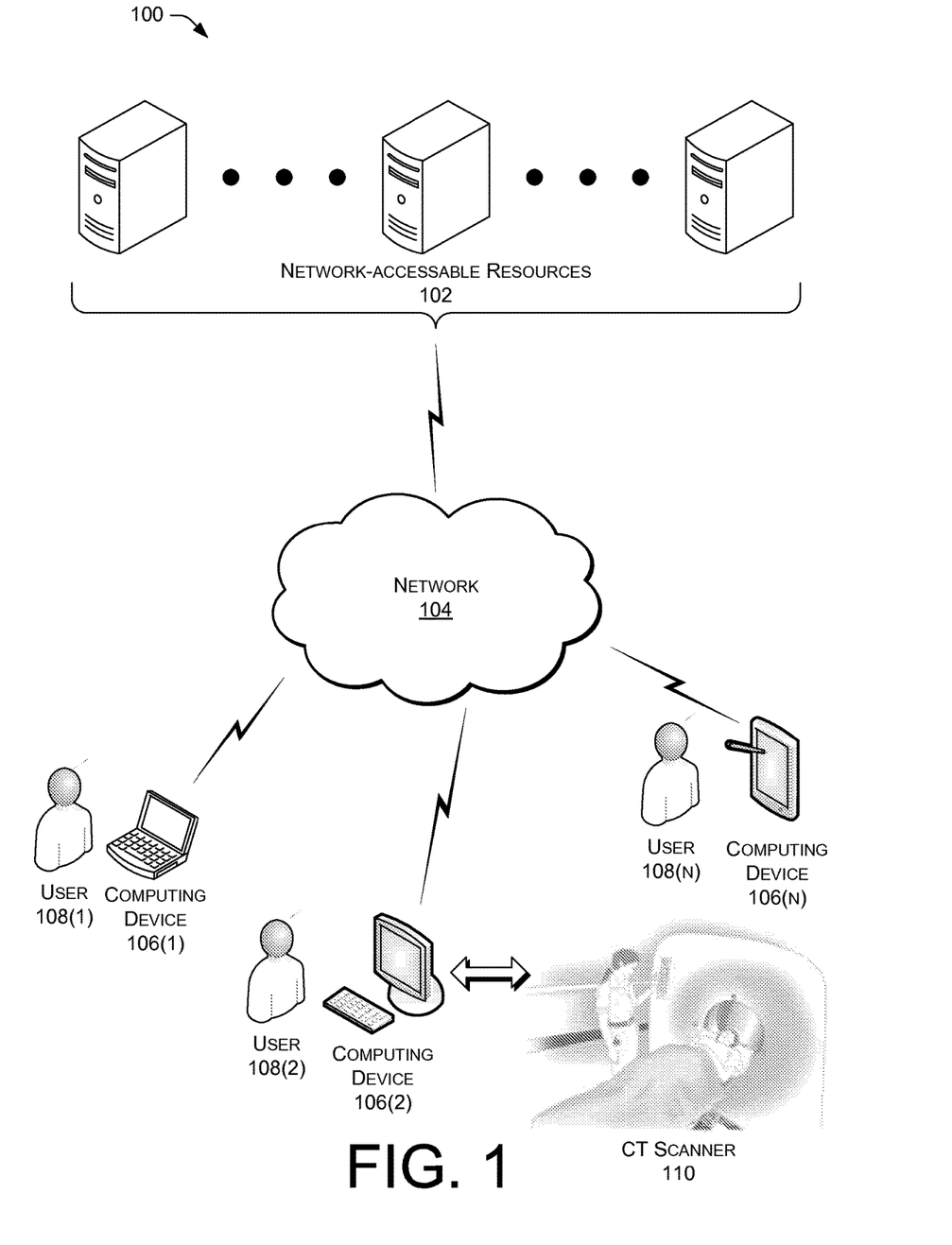
FIG. 1 shows an illustrative architecture for rendering and distributing CT scan images.

FIG. 1 shows an illustrative architecture 100 for implement techniques to provided physically remote and network-accessible (i.e., "cloud-based") rendering of tomographic image data comprising slices of an imaged three-dimensional object. Network-accessible resources (e.g., network server computers) 102 are connected to one to n computing devices 106(1)-106(n) accessed by users 108(1)-108(n) respectively. One or more of the computing devices 106 may be communicatively coupled to a CT scanner 110. The users 108 may be physicians, patients, engineers, archeologists, etc. The users 108 may view data from the CT scanner 110 that is rendered into images by the network-accessible resources 102 on one of the computing devices 106. The computing devices 106 may include any type of computing device such as a desktop computer, a laptop computer, a tablet computer, a mobile phone, a personal digital assistant, a set top box, a game console, a thin client, etc. Although described in this disclosure primarily as a distributed system, the components and techniques described herein may also be implemented in a single computing device potentially without network connections or as a local system in which case the network-accessible resources 102 would not necessary be physically remote from other components of this system.

Figure 2:
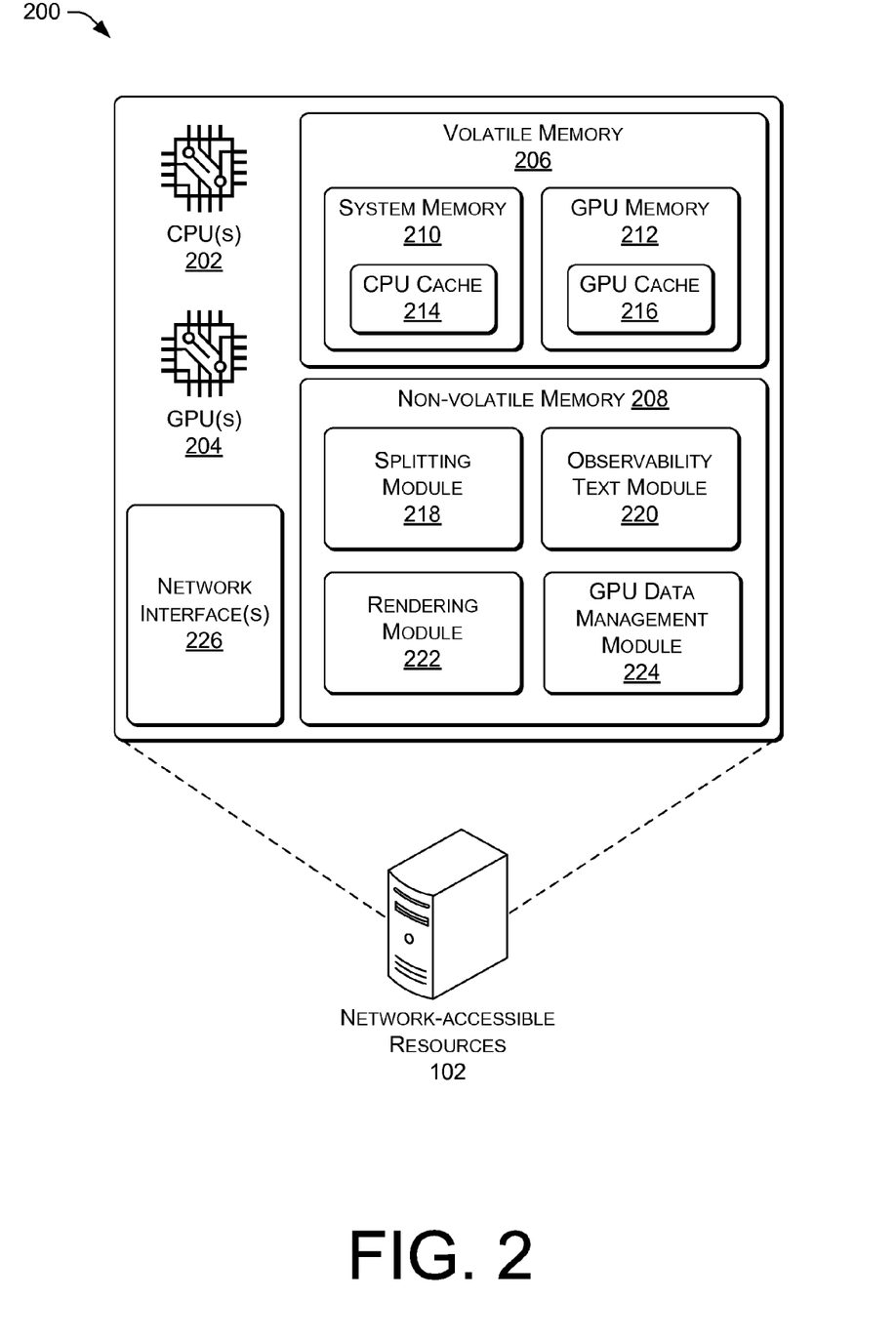
FIG. 2 shows the network-accessible resources of FIG. 1 in greater detail.

FIG. 2 shows an illustrative block diagram 200 of components in the network-accessible resources 102. The network-accessible resources 102 may include one or more central processing units (CPU) 202 and one or more graphics processing units (GPU) 204.

The network-accessible resources 102 may also include one or more types of memory such as volatile memory 206 and non-volatile memory 208. Volatile memory 206 may include system memory 210 and GPU memory 212. Both the CPU 202 and the GPU 204 may have associated memory caches in the volatile memory 206. The system memory 210 may include a CPU memory cache 214 and the GPU memory 212 may include a GPU cache 216.

The non-volatile memory 208 may include a splitting module 218, an observability test module 220, a rendering module 222, and a GPU data management module 224. Each of these is discussed below in greater detail. A network interface 226 may be configured to send and receive data, such as a rendered image, to other computing devices such as the computing device 106 shown in FIG. 1.

In some implementations, the non-volatile memory 208 may be implemented in whole or in part as a hard-disk drive (HDD) such as, for example, a 1 TB SATA II HDD, and the system memory 210 may be implemented as random access memory such as, for example, 12 GB DDR3. The GPU memory 212 may be implemented as random access memory such as for example 1 GB to 6 GB of DDR5. The CPU(s) 202 may be implemented in whole or in part using Intel Core i7, AMD Athlon 64×4, and/or AMD Phenom II×4 CPUs. The GPU(s) 204 may be implemented in whole or in part using nVidia GeForce GTX560Ti, GTX480, GTX590, and/or nVidia Tesla M2050 or M2090 GPUs.

The splitting module 218 may split a voxel dataset or subset of a voxel dataset maintained in volatile memory 206 into a plurality of macro blocks and save the macro blocks to a plurality of image data files stored in the non-volatile memory 208. In some implementations, the image data files may be stored in parallel on a plurality of non-volatile memory 208 devices.

The observability test module 220 selects potentially observable macro blocks by testing macro block in a list for whether the block is visible and whether the block is in-frame. Potentially observable macro blocks meet both of these tests and are provided to the rendering module 222.

The rendering module 222 renders an image from the set of macro blocks provided to the rendering module from a plurality of data storage devices. In some implementations this rendering may be performed in parallel on the macro blocks.

The GPU data management module 224 may be configured to determine if the GPU cache 216 is full. When the GPU cache 216 is full, the GPU data management module 224 may delete the contents of a random processor register in the GPU cache 216 to create free space to render additional voxel data.

Figure 3:
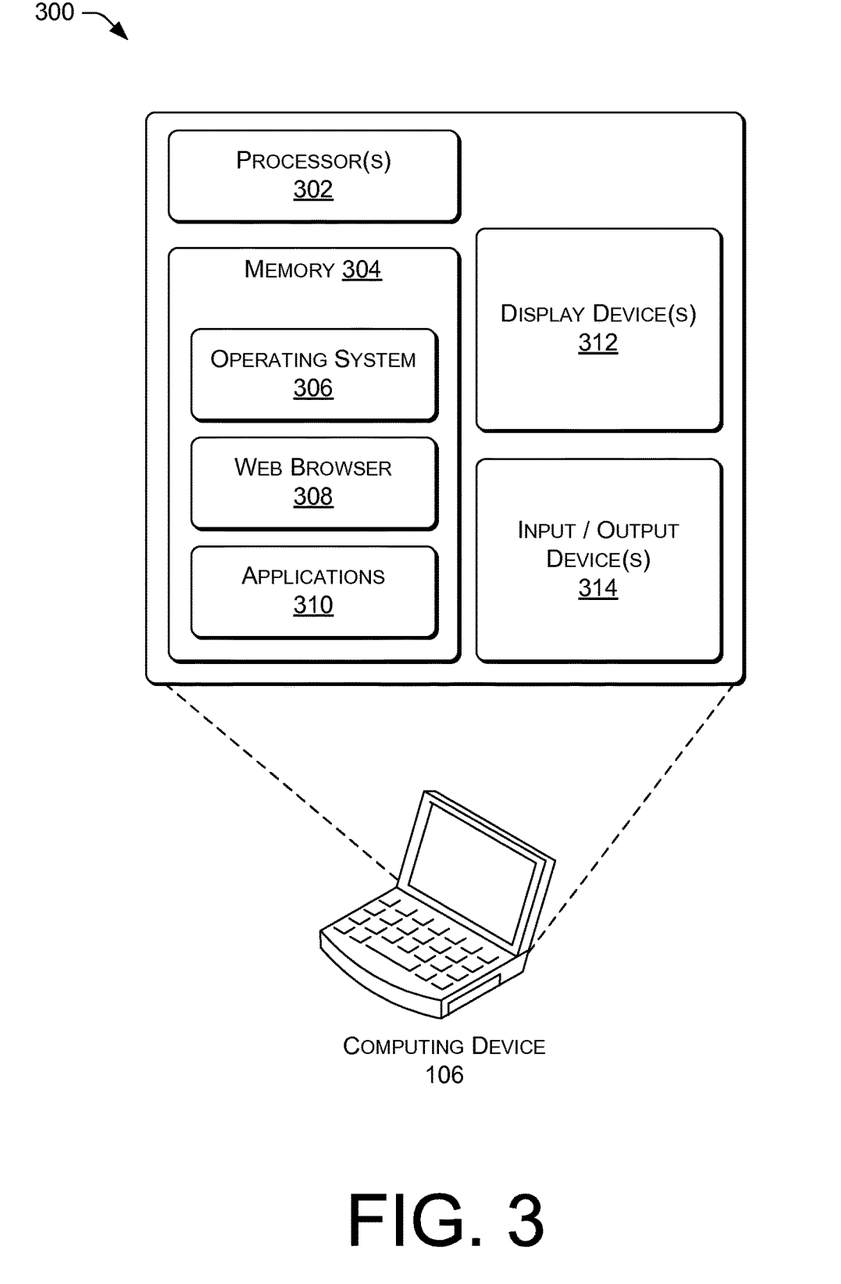
FIG. 3 shows the computing device of FIG. 1 in greater detail.

FIG. 3 shows an illustrative block diagram 300 of one of the computing devices 106 of FIG. 1. The computing device 106 may include one or more processors 302 and a memory 304. The memory 304 may contain an operating system 306, a web browser 308, and one or more other applications 310. The computing device 106 may also be equipped with one or more display devices 312 that may be implemented as stereoscopic display systems or autostereoscopic display system for showing three-dimensional images. In some implementations, the web browser 308 may provide an interface for the user 108 to view and interact with CT scan images, other two-dimensional, and/or three-dimensional images. The computing device 106 may also include other input and output devices 314 such as a keyboard, mouse, speakers, and the like.

Large Dataset Management

CT scanners 110 and other types of tomographic imaging approaches generate large image datasets comprising a series of two-dimensional image files that are "slices" of the three-dimensional scanned object. Similar image datasets may be generated through other scanning techniques such as MRI and may also be generated by virtual computer simulations. These datasets may be difficult to manage due to the large quantity of data and size of the files.

Files from the CT scanner 110 may be formatted according to the DICOM standard. The DICOM standard includes a file format definition and a network communications protocol and may also include information specific to medical applications such as a patient's name, referring physician's name, etc. The communication protocol is an application protocol that uses TCP/IP to communicate between systems. Dataset sizes for CT scans may be several gigabytes and may grow in the future as CT scanner resolution increases.

Figure 4:
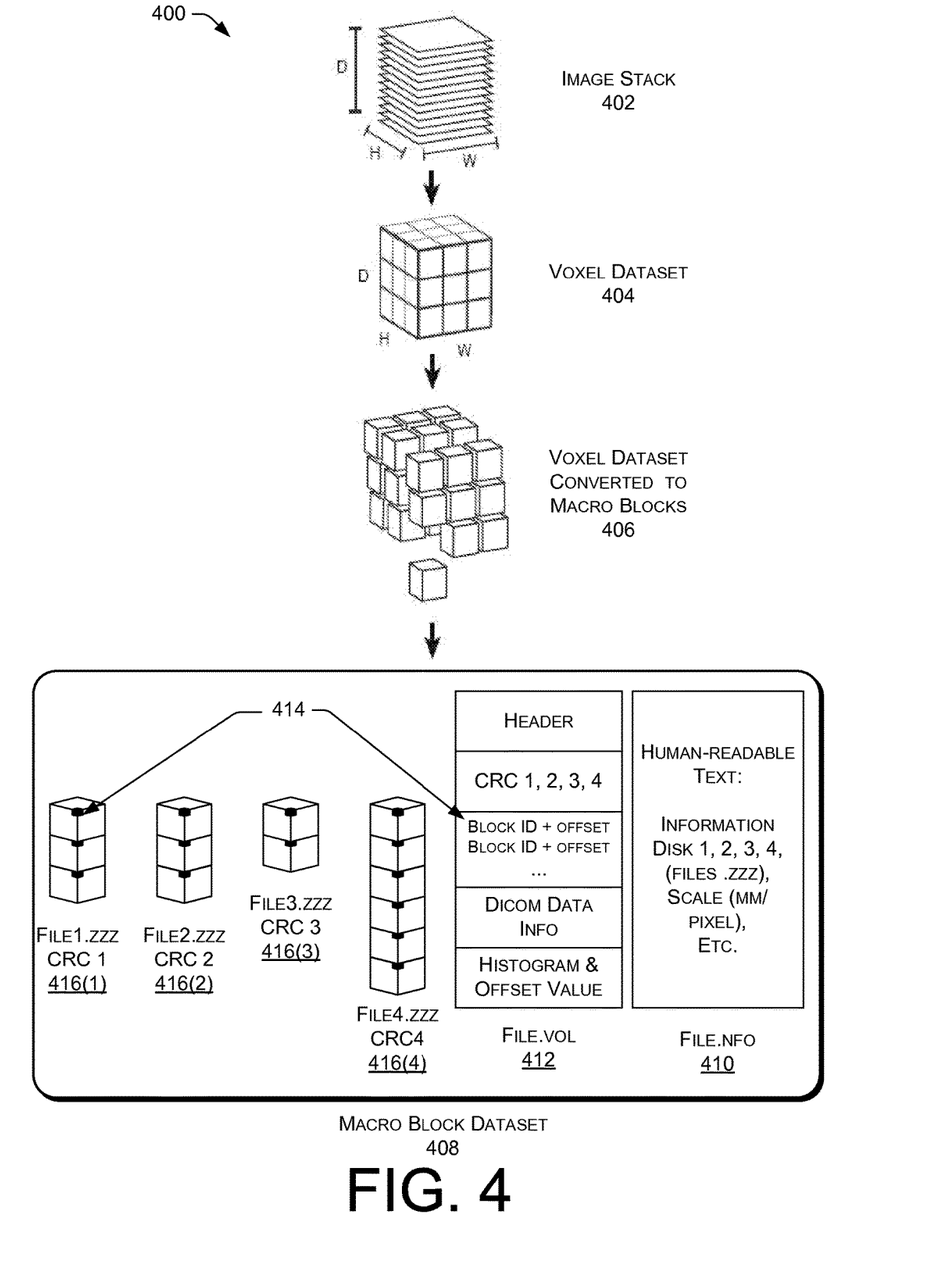
FIG. 4 shows an illustrative description of the structure of the dataset as it is converted from input data into a macro block dataset.

FIG. 4 shows an illustrative description 400 of the different structures into which the graphical dataset is transformed as it is converted from input data (such as, for example, DICOM-format data generated by a CT scanner 110) into a macro block dataset saved to non-volatile memory 208 in the network-accessible resources 102. The input dataset may be a series of two-dimensional images, or image stack dataset 402 representing one or more scanned objects. The image stack dataset 402 is reconstructed as a three-dimensional voxel dataset 404. Once partitioned, the voxel dataset 404 may be partitioned into a collection of macro blocks 406.

The collection of macro blocks 406 may be stored as a macro block dataset 408 on hard disk or other storage device or devices as a group of six files. In some implementations there may be a greater or lesser number of files. The group of files may include an information (*.nfo) file 410 that may include human readable information in as text such as ASCII or extended ASCII text that contains information about the other files in the group.

Additionally, the group of files may include a volume (*.vol) file 412 that defines a system design layout and selects appropriate translator modules. The volume file may also include a header, cyclic redundancy check (CRC) data value for each image data file, block identifier (ID) and offset 414, DIACOM data and/or other patient information, and data histogram.

In this illustrative example, four image data files 416(1)-416(4) are shown. The image files 416 may be indicated by the file extension (*.zzz). The image data files 416 contain voxels which represent the image data produced by a three-dimensional imaging unit such as the CT scanner 110. Each macro block may be associated with 256×256×256 constituent voxels.

However, more or fewer than four image files 416 may be used. The image files 416 may be stored in the volatile memory 206 or the non-volatile memory 208 of the network-accessible resources 102. The voxels are volume elements that represent a value on a regular grid in three-dimensional space. The position of a voxel may be inferred based upon a position relative to other voxels (i.e., a position in the data structure that makes up a single volumetric image). The image data files 416 may also be compressed to reduce file size. The cyclic redundancy check (CRC) value for each image data file 416 may be stored in the volume file 412, so that data integrity of the respective image data files 416 may be checked before loading the image data files 416. The location of each macro block in the image data files 416 is recorded in the volume file 412 using a reference comprising the block identifier and offset 414 within the image data file 416. The data histogram in the volume file 412 may be a cumulative histogram calculated from the voxels from the dataset 406.

The voxels in the image data files 416 may be dynamically loaded as needed. In some implementations, multiple voxels are loaded at the same time. A list of the macro blocks associated with the voxel dataset 406 may be loaded into system memory 210 without loading the constituent voxels themselves into memory. The macro block data structure may also contain attributes that summarize the opacity range of constituent voxels. To determine which voxels in the image data files 416 should be loaded, a list of all of the macro blocks may be tested to identify whether they are visible and in-frame in the desired rendered projection of the three-dimensional object.

Illustrative Processes

Figure 5:
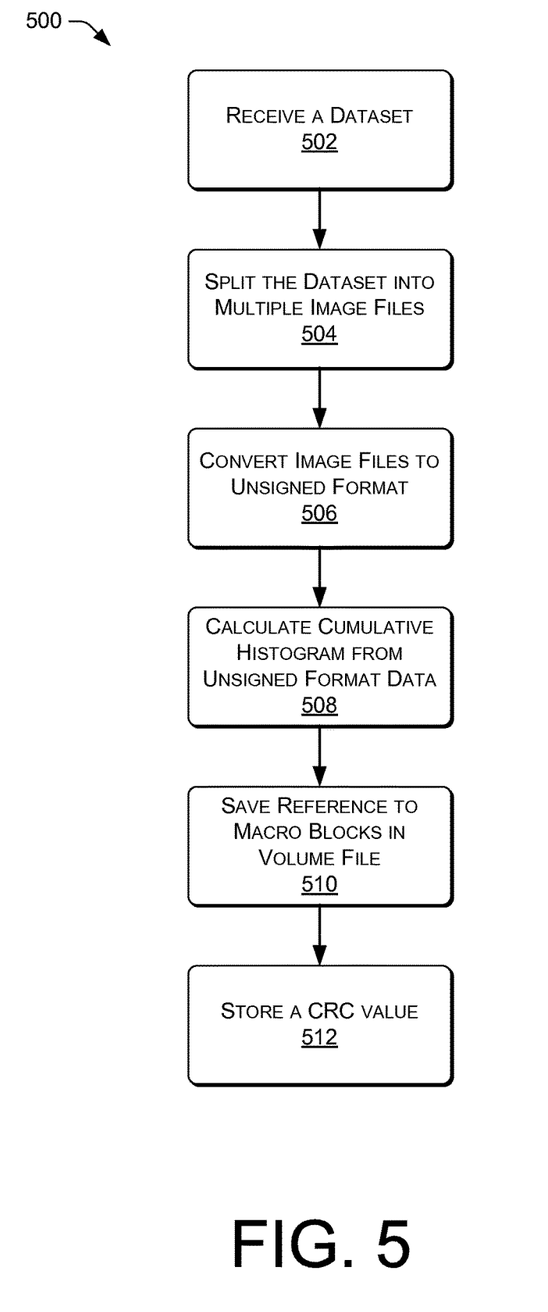
FIG. 5 shows an illustrative procedure for converting input data into a macro block dataset.
Figure 6:
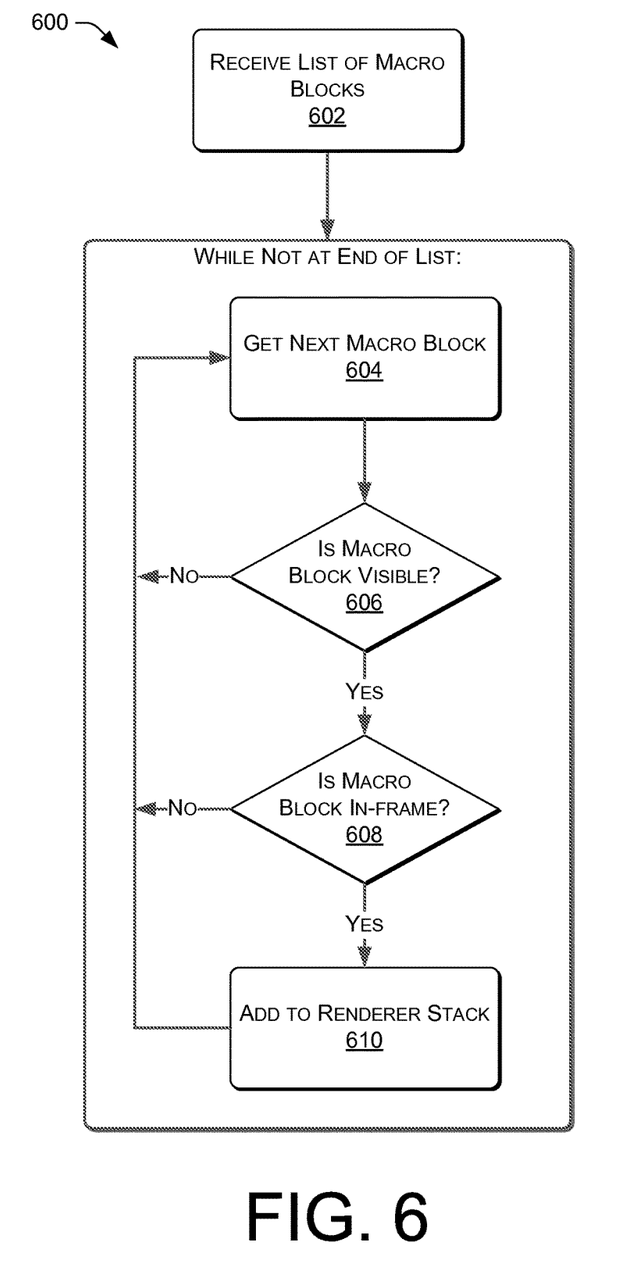
FIG. 6 shows an illustrative procedure for using a visibility and in-frame test to populate a rendering stack.
Figure 7:
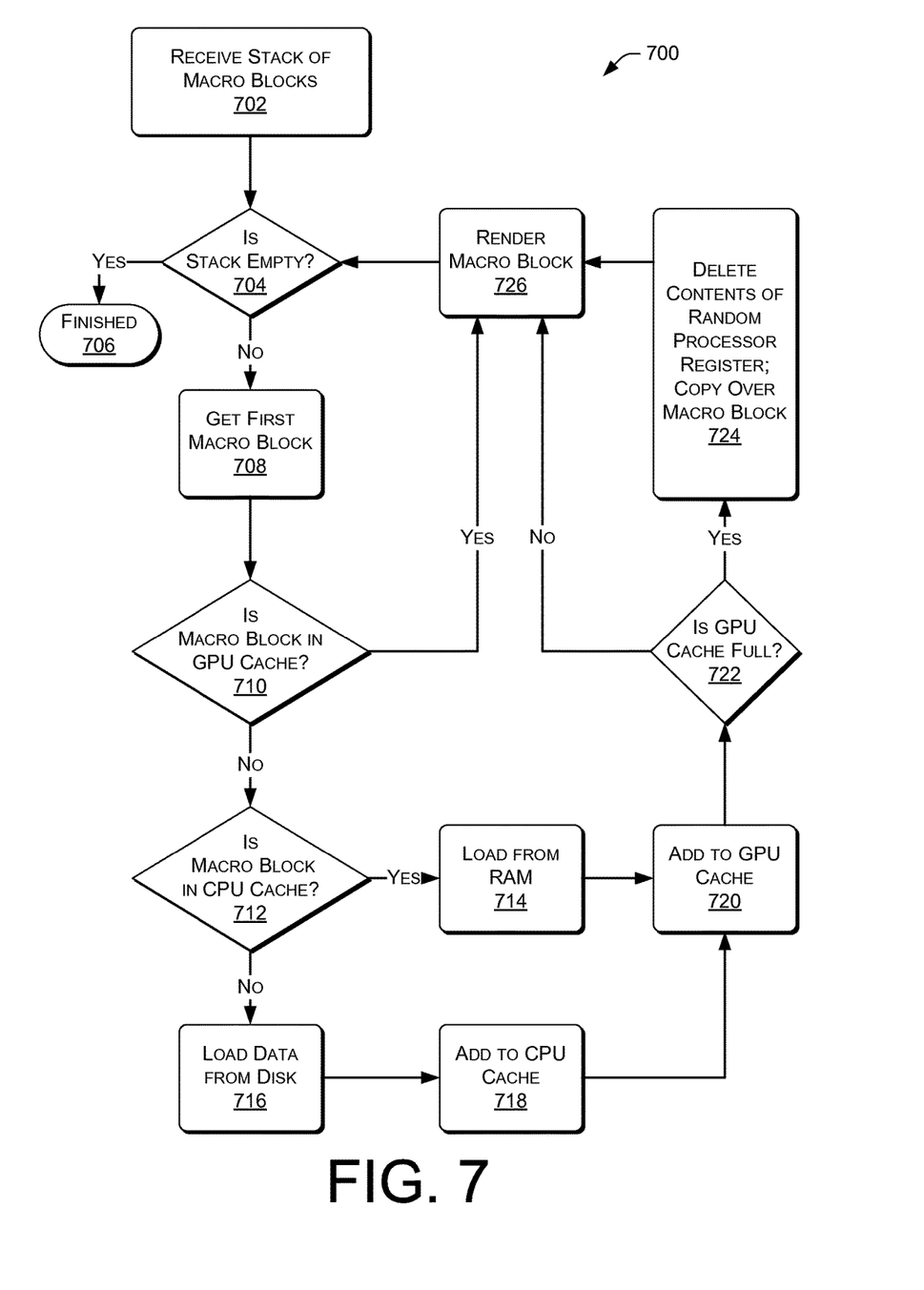
FIG. 7 shows an illustrative procedure for processing the rendering stack to achieve a rendered projection of a three-dimensional object.

Processes 500, 600, and 700 are illustrated as a collection of blocks in logical flow graphs, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

FIG. 5 shows an illustrative procedure 500 for converting input data into a macro block dataset saved to non-volatile memory 208.

At 502, an image stack dataset 402 representing one or more scanned objects is received, and is reconstructed as a three-dimensional voxel dataset 404.

At 504, the dataset received at 502 is parsed into a collection of macro blocks 406 and split into multiple image data files 416, each containing multiple macro blocks. In some implementations, the dataset may be split into four image data files 416(1)-416(4) saved to disk in the network-accessible resources 102.

At 506, the macro blocks are converted to an unsigned short (e.g., unsigned 16-bit) format.

At 508, a cumulative histogram is calculated using the data from the unsigned short format 506.

At 510, the location of each macro block in the image data files 416 is recorded in the volume file 412 using a reference comprising a block ID and offset 414 within the respective image data file 416(1)-414(4).

At 512, a cyclic redundancy check (CRC) value for each image data file 416 may be stored in the volume file 412, so that data integrity may be checked before loading the image data files 416.

FIG. 6 shows an illustrative procedure 600 for using a visibility text and an in-frame test to populate a rendering stack that may be limited to macro blocks with constituent voxels that will be visible in the desired projection.

At 602, a list of all macro blocks is received. The macro block attributes including a summary of the constituent voxels may be loaded into memory. In some implementations, the actual constituent voxels in the image data files are not loaded into memory. Loading only the summaries and the block attributes may reduce the demand on computing resources. By loading only the constituent voxels that may be observable in the rendered image (i.e., based on the visibility test and the in-frame test), there may be an improvement in loading speed and much larger input datasets can be processed.

Macro blocks in the list of macro blocks 602 are tested in sequence to identify those macro blocks that will ultimately be included in the final rendered image. This process could be implemented as a while-loop, such that the current position in the list changes as the test is applied to each macro block in sequence. At 604, a macro block at the current position in the list is received from the list of macro blocks 602, and this block becomes the current macro block for subsequent analysis.

At 606, the current macro block is tested to determine if it will be visible or invisible (e.g., not rendered) in the rendered image. The macro block summary of constituent voxels includes a minimum and maximum voxel value within the current block. These values are compared to a minimum and maximum thresholds defining the bounds for visible voxels in the projection to be rendered. The macro block is invisible if the minimum and maximum values for the current macro block fall outside the bounds for the rendered projection. Additionally, if the current values for minimum and maximum are equal, the macro block is "empty" because all of the constituent voxels have the same value. Voxels associated with "empty" macro blocks do not need to be loaded from the image data files 416, because no additional information is provided by the voxels on disk. If the current macro block is determined to be invisible then process 600 proceeds along the "no" path and returns to 604 where the next macro block is tested.

If a macro block is visible and passes the visibility test in 606, process 600 proceeds along the "yes" path to 608 and the current macro block is tested for whether the constituent voxels are in-frame or not. If the constituent voxels of the current macro block are not visible then process 600 follows the "no" path and returns to 604 where the next macro block is tested. The macro block is associated with attributes that identify the maximum range of the locations of the constituent voxels in a three-dimensional regular grid. If the range of the current macro block is completely outside of the part of the grid that is within the viewing frame for the projection to be rendered (i.e., it would be "off screen" when presented on a display), the macro block fails the in-frame test and process 600 proceeds along the "no" path from 608 and returns to 604 to test/check another macro block. If a macro block passes the in-frame test in 608, process 600 proceeds along the "yes" path to 610.

At 610 the macro block is added to the renderer stack 610. Thus, the render stack may include macro blocks that are identified as being visible at 606 and being in-frame at 608. Excluding other macro blocks from the renderer stack minimizes the use of computational resources by reducing the number of voxels that will need to be loaded from disk.

FIG. 7 shows an illustrative procedure 700 for processing the contents of the rendering stack, such as the rendering stack generated at 610 in FIG. 6, to achieve a rendered projection of a three-dimensional object.

Before initiating the process 700 for processing the rendering stack, the integrity of the data in the saved image files 416 may be verified by comparing the CRC values to the previously saved CRC values in the volume file 412. All or part of process 700 may be executed simultaneously, in parallel, using multiple CPUs and GPUs.

At 702, a stack of macro blocks is received.

At 704, it is determined if the stack of macro blocks received at 702 is empty or if the stack contains macro blocks containing image data. If the stack is empty, there is nothing left to render, so process 700 proceeds along the "no" path to 706 and process 700 finishes. If the stack of macro blocks is not empty and contains one or more macro blocks with image data then process 700 proceeds along the "yes" path to 708.

At 708, the first macro block is removed from the stack of macro blocks received at 702 for analysis.

At 710, the GPU memory cache 216 is checked to see if the macro block is already present in the GPU memory cache 216—if present, process 700 follows the "yes" path to 726; if not present, process 700 follows the "no" path to 712.

At 712, the CPU memory cache 214 is checked to see if the macro block is present in the CPU memory cache 214—if present, process 700 follows the "yes" path to 714; if not present, process 700 follows the "no" path to 716.

At 714, since the macro block is not present in the GPU memory cache 216, the constituent voxel data is copied from the volatile memory 206 (e.g. RAM).

At 716, since the macro block is not present in the CPU memory cache 214, the macro block constituent voxel data is loaded from the corresponding image data file 416 at 716. In some implementations, the macro blocks may be loaded by reading from multiple (e.g., four) non-volatile memory devices, for example non-volatile memory 208, at the same time.

At 718 the voxel data read in 716 is added to the CPU memory cache 214.

At 720, the macro block voxel data is copied from the CPU memory cache 214 to the GPU memory cache 216.

At 722, the GPU memory cache 216 is checked to determine if it is full. If the GPU memory cache 216 is full, process 700 follows the "yes" path to 724. If the GPU memory cache 216 is not full, process 700 follows the "no" path to 726.

At 724, the contents of a random processor register of the GPU memory cache 216 are deleted and the voxel data from the current macro block are coped to the random process register.

At 726, whether arrived at from 710, 722, or 724, the voxel data that is in the GPU memory cache 216 is rendered. Process 700 then returns to 704 and repeats until the stack of macro blocks no longer contains additional macro blocks.

The image created by rendering individual macro blocks at 726 from the entire stack of macro blocks received in 702 may be viewed by a user 108 on the display device(s) 312 of the computing device 106.

Conclusion

Although the subject matter of this disclosure has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. A method for providing network-accessible processing of complex image data comprising:
    splitting, by one or more processors of a network-accessible resource including at least one graphics processing unit (GPU), a data set of three-dimensional image data generated from a series of two-dimensional image data files depicting slices of a three-dimensional object into a plurality of macro blocks comprising Volumetric Picture Elements (voxels) arranged in a three-dimensional regular grid;
    saving the plurality of macro blocks to a plurality of files stored on a plurality of computer-readable data storage devices accessible to the network-accessible resource;
    determining that a GPU cache of the corresponding at least one GPU is full;
    deleting contents of a random processor register of the GPU cache in response to the determining that the GPU cache is full;
    identifying, by the network-accessible resource, from the plurality of macro blocks a subset of observable macro blocks that include one or more constituent voxels having the characteristics of: (i) an opacity value between a minimum and maximum threshold defining bounds for visible voxels in a rendered projection of the three-dimensional image data and (ii) a location within a range of locations in the three-dimensional regular grid that is included within a viewing frame for the rendered projection of the three-dimensional image data, wherein a macro block that only contains voxels located outside the range of locations in the three-dimensional regular grid that is included within the viewing frame is not included in the subset of the observable macro blocks;
    determining and recording, by the network-accessible resource, a cyclic redundancy check (CRC) value for one or more of the plurality of files, and comparing the CRC value for the one or more of the plurality of files to a previously recorded CRC value to check data integrity before transferring the subset of observable macro blocks to the rendering module;
    subsequent to the identifying, transferring the subset of the observable macro blocks from the plurality of files to a rendering module of the network-accessible resource; and
    sending, from the network-accessible resource, a rendered image generated from the subset of observable macro blocks to a web browser interface of a computing device that is physically remote from the network-accessible resource.

2. The method of claim 1, wherein the subset of observable macro blocks is distributed within one or more visible layers of the rendered projection.

3. The method of claim 1, wherein macro blocks of the plurality of macro blocks further comprise at least one of attributes that summarize the maximum and minimum opacity values of the constituent voxels or information about the color ranges of constituent voxels.

4. The method of claim 1, wherein each of the plurality of files is stored in a separate one of the plurality of computer-readable data storage devices.

5. The method of claim 1, further comprising rendering in parallel, by the rendering module, the rendered image that is a two-dimensional projection of the subset of the observable macro blocks transferred to the rendering module.

6. The method of claim 1, wherein the three-dimensional image data comprises slices of a three-dimensional object.

7. The method of claim 1, wherein the three-dimensional image data comprises image data generated at least in part by a computed tomography (CT) scanner.

8. The method of claim 1, wherein the plurality of files are compressed.

9. A computing device comprising:
one or more processors comprising at least one central processing unit (CPU) and at least one graphics processing unit (GPU);
a plurality of computer-readable data storage devices coupled to the one or more processors storing an input data set comprised of a series of two-dimensional image data files depicting slices of a three-dimensional object;
a computer-readable memory coupled to the one or more processors;
a splitting module maintained in the memory and configured to perform acts comprising:
splitting at least a portion of the input data set into a plurality of macro blocks; and
saving the plurality of macro blocks to a plurality of files stored on the plurality of computer-readable data storage devices;
a GPU data management module maintained in the memory and configured to perform acts comprising:
determining whether a GPU cache is full; and
deleting the contents of a random processor register of the GPU cache when the GPU cache is full; and
an observability test module maintained in the memory and configured to perform acts comprising:
identifying from the plurality macro blocks a subset of macro blocks that contain one or more constituent voxels having the characteristics of: (i) an opacity value between a minimum and maximum threshold defining bounds for visible voxels in a rendered projection of an imaged object and (ii) a location within a range of locations in a three-dimensional regular grid that is included within a viewing frame for the rendered projection of the imaged object, wherein a macro block that only contains voxels located outside the range of locations in the three-dimensional regular grid that is included within the viewing frame is not included in the subset of the observable macro blocks; and
subsequent to the identifying, providing the subset of observable macro blocks to a rendering module.

10. The computing device according to claim 9, further comprising one or more network interfaces coupled to the one or more processors, and configured to send the rendered projection of the imaged object to a remote computing device.

11. The computing device according to claim 9, wherein the rendering module is maintained in the memory and configured to render an image from the subset of observable macro blocks, wherein the rendering module operates in parallel on macro blocks provided to the rendering module from the plurality of computer-readable data storage devices.

12. The computing device according to claim 9, wherein the macro blocks comprise attributes that summarize the maximum and minimum opacity values of constituent voxels and information about the color ranges of constituent voxels.

13. A non-transitory computer-readable storage media containing instructions that, when executed by a processor, instruct the processor to perform acts comprising:
receiving three-dimensional image data comprising a series of two-dimensional image slices of a three-dimensional object;
splitting the three-dimensional image data into a plurality of macro blocks comprising Volumetric Picture Elements (voxels) arranged in a three-dimensional regular grid and wherein the plurality of macro blocks is distributed within one or more visible layers of a rendered projection of the three-dimensional image data;
saving the plurality of macro blocks to a plurality of files stored on a plurality of computer-readable data storage devices;
determining and recording cyclic redundancy check (CRC) values for one or more of the plurality of files;
comparing the CRC values of the one or more of the plurality of files to previously recorded CRC values of the same one or more of the plurality of files, wherein when the CRC values of the one or more of the plurality of files differ from the previously recorded CRC values, the one or more of the plurality of files are not rendered;
identifying from the plurality of macro blocks a subset of observable macro blocks that include one or more constituent voxels having the characteristics of: (i) an opacity value between a minimum and maximum threshold defining bounds for visible voxels in the rendered projection of the three-dimensional image data and (ii) a location within a range of locations in the three-dimensional regular grid that is included within a viewing frame for the rendered projection of the three-dimensional image data;
subsequent to the identifying, transferring the subset of observable macro blocks from the plurality of files to a rendering module;
rendering, by the rendering module, an image that is a two-dimensional projection of the set of macro blocks transferred to the rendering module; and
sending a rendered image generated from the two-dimensional projection via one or more network interfaces to a web browser of a remote computing device.

14. The non-transitory computer-readable storage media of claim 13, wherein a macro block that only contains voxels located outside the range of locations in the three-dimensional regular grid that is included within the viewing frame is not included in the subset of the observable macro blocks.

15. The non-transitory computer-readable storage media of claim 13, wherein the macro blocks comprise attributes that summarize the maximum and minimum opacity values of constituent voxels and information about the color ranges of constituent voxels.

16. The non-transitory computer-readable storage media of claim 13, wherein the plurality of files are compressed.

* * * * *